United States Patent
Shi et al.

(10) Patent No.: US 6,929,817 B2
(45) Date of Patent: *Aug. 16, 2005

(54) SLOWLY DIGESTIBLE STARCH PRODUCT

(75) Inventors: Yong-Cheng Shi, Hillsborough, NJ (US); Xiaoyuan Cui, Belle Mead, NJ (US); Anne M. Birkett, Somerville, NJ (US); Michael G. Thatcher, Bridgewater, NJ (US)

(73) Assignee: National Starch & Chemical Investment Holding Corporation, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/145,264

(22) Filed: May 14, 2002

(65) Prior Publication Data

US 2003/0215562 A1 Nov. 20, 2003

(51) Int. Cl.$^7$ .................... C08B 30/00; A23L 1/0522
(52) U.S. Cl. ............................ 426/661; 127/32
(58) Field of Search ............... 127/32, 71; 426/19, 426/28, 64, 52, 661

(56) References Cited

U.S. PATENT DOCUMENTS

| | | | |
|---|---|---|---|
| 3,490,742 A | 1/1970 | Nichols et al. | |
| 3,622,677 A | 11/1971 | Short et al. | |
| 3,632,475 A | 1/1972 | Sugimoto et al. | |
| 3,881,991 A | 5/1975 | Kurimoto et al. | |
| 4,072,535 A | 2/1978 | Short et al. | |
| 4,384,005 A | 5/1983 | McSweeney | |
| 4,551,177 A | 11/1985 | Trubiano et al. | |
| 4,971,723 A | 11/1990 | Chiu | |
| 5,051,271 A | 9/1991 | Iyengar et al. | |
| 5,194,284 A | 3/1993 | Chiu et al. | |
| 5,281,276 A | 1/1994 | Chiu et al. | |
| 5,395,640 A | 3/1995 | Harris et al. | |
| 5,409,542 A | 4/1995 | Henley et al. | |
| 5,409,726 A | 4/1995 | Stanley et al. | |
| 5,468,286 A | 11/1995 | Wai-Chiu et al. | |
| 5,585,114 A | 12/1996 | Besemer et al. | |
| 5,629,018 A | 5/1997 | Besemer et al. | |
| 5,776,887 A | 7/1998 | Wibert et al. | |
| 5,849,090 A | 12/1998 | Haralampu et al. | |
| 5,962,047 A | 10/1999 | Gross et al. | |
| 6,010,717 A | 1/2000 | Arends-Scholte et al. | |
| 6,086,917 A | 7/2000 | Trubiano et al. | |
| 6,090,594 A | 7/2000 | Kettlitz et al. | |
| 6,248,375 B1 | 6/2001 | Gilles et al. | |
| 2002/0012733 A1 | 1/2002 | Kester et al. | |

FOREIGN PATENT DOCUMENTS

| | | |
|---|---|---|
| EP | 0 499 648 | 12/1993 |
| EP | 0 486 936 | 8/1994 |
| EP | 0 512 249 B1 | 3/1999 |
| EP | 0 688 872 | 3/1999 |
| EP | 0 692 252 B1 | 4/2001 |
| EP | 0 846 704 B1 | 3/2002 |
| EP | 0 747 397 | 8/2003 |
| WO | WO 93/03629 | 3/1993 |
| WO | WO 97/31627 | 9/1997 |
| WO | WO 99/02042 | 1/1999 |
| WO | WO 99/09066 | 2/1999 |
| WO | WO 00/55209 | 9/2000 |
| WO | WO 01/17370 | 3/2001 |
| WO | WO 01/21011 | 3/2001 |
| WO | WO 01/64255 | 9/2001 |

OTHER PUBLICATIONS

Guraya et al., "Effect of Enzyme Concentration and Storage Temperature on the Formation of Slowly Digestible Starch from Cooked Debranched Rice Starch", Starch/Starke 53 (2001), pp. 131–139.

FAO Food and Nutrition Paper 66, "Carbohydrates in human nutrition", Chapter 4—The Role of the Glycemic Index in Food Choice, pp. 25–30, Report from Apr. 14–18, 1997.

Englyst et al., "Classification and measurement of nutritionally important starch fractions", European Journal of Clinical Nutrition (1992) 46 (Suppl. 2), S33–S50.

Guraya et al., "Effect of Cooling, and Freezing on the Digestibility of Rice Starch and Physical Properties of the Resulting Material", Starch/Stärke 53 (2001), pp. 64–74.

*Primary Examiner*—Keith Hendricks
(74) *Attorney, Agent, or Firm*—Karen G. Kaiser

(57) ABSTRACT

This patent pertains to a slowly digestible starch prepared by debranching amylose-containing starches, particularly by pullulanase or isoamylase. Such slowly digestible starches are useful in edible products, including nutritional supplements.

11 Claims, No Drawings

SLOWLY DIGESTIBLE STARCH PRODUCT

BACKGROUND OF THE INVENTION

The present invention relates to a slowly digestible starch product prepared by enzymatically debranching amylose-containing starches and allowing the resultant linear chains to crystallize to a highly crystalline form.

Starch is a major source of energy in the typical American diet. Refined starches are mostly eaten cooked, and in this form generally have a high glycemic index, being quickly and substantially digested. Some refined starches resist enzymatic hydrolysis in the small intestine, such that the starch is not substantially broken down until it reaches the large intestine where it is utilized by resident microorganisms (resistant starch).

A need has been recognized for a slowly digestible starch, one which provides the consumer with glucose over an extended time period. Such slowly digestible starch would thus be useful for both food and drug applications.

Such slowly digestible starch would be an excellent carbohydrate for use in foods, including medical foods and dietary supplements, for both diabetic and prediabetic individuals. Such slowly digestible starch would also be useful for healthy individuals wishing to moderate their glucose response or achieve sustained energy release via consumption in foods.

Research literature indicates a role for slowly digestible starches in health, as a result of glucose release over an extended time period. Research suggests health-related benefits may include increased satiety for longer time periods (i.e. for use in weight management), sustained energy release (i.e. for enhancing athletic performance including training), and improvements in concentration maintenance and memory.

Such slowly digestible starches could also be useful as drugs, e.g. for reducing the risk of developing diabetes. Further, the slowly digestible starches may be useful for the treatment of hyperglycemia, insulin resistance, hyperinsulinemia, dyslipidemia, and dysfibrinolysis. It may also be useful for treating obesity.

Surprisingly, it has now been discovered that a slowly digestible starch may be prepared by enzymatically debranching amylose-containing starches to result in a mixture of long and short linear chains.

SUMMARY OF THE INVENTION

This patent pertains to a slowly digestible starch product prepared by debranching amylose-containing starches and allowing the resultant highly linear chain starch to crystallize to a highly crystalline form. The slowly digestible starches provide sustained energy release with a low Glycemic Index.

As used herein, the term rapidly digestible starch is intended to mean a starch or portions thereof which are digested within 20 minutes of digestion as measured by Englyst et al, 1992 (Englyst et al, European Journal of Clinical Nutrition, 1992, 46, S33–S50).

As used herein, the term resistant starch is intended to mean a starch, or the fraction thereof, which is not digested in the small intestines as measured by Englyst et al, 1992 (Englyst et al, European Journal of Clinical Nutrition, 1992, 46, S33–S50).

As used herein, the term slowly digestible starch is intended to mean a starch, or the fraction thereof, which is neither rapidly digestible starch or resistant starch.

Fully or completely debranched starch, as used herein, is intended to mean that which theoretically comprises 100%, by weight, of linear chains and, in practice, that which is so highly debranched that further enzyme activity produces no measurable change in the percentage of linear chains.

Glycemic Index, as used herein, is intended to mean the incremental area under the blood glucose response curve of a 50 g carbohydrate portion of a test food expressed as a percent of the response to the same amount of carbohydrate from a standard food taken by the same subject. Typically, carbohydrate is on an available basis and either white bread or glucose is used as the standard food. See Carbohydrates in human nutrition, FAO Food and Nutrition Paper 66, Report of a Joint FAO/WHO Expert Consultation, Rome, 14–18 April 1997.

DETAILED DESCRIPTION OF THE INVENTION

This patent pertains to a slowly digestible starch product prepared by enzymatically debranching amylose-containing starches and allowing the resultant linear chains to crystallize to a highly crystalline form. The slowly digestible starches provide sustained energy release with a low Glycemic Index.

Starch, as used herein, is intended to include all starches derived from any native source, any of which may be suitable for use herein. A native starch as used herein, is one as it is found in nature. Also suitable are starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

Typical sources for the starches are cereals, tubers, roots, legumes and fruits. The native source can be any amylose-containing variety of corn (maize), pea, potato, sweet potato, banana, barley, wheat, rice, oat, sago, amaranth, tapioca, arrowroot, canna, sorghum and high amylose varieties thereof. As used herein, the term "amylose-containing" is intended to include a starch containing at least about 10% by weight amylose. As used herein, the term "high amylose" is intended to include a starch containing at least about 40%, particularly at least about 70%, more particularly at least about 80% by weight amylose. Particularly suitable are non-high amylose starches (ie. about 10 to about 40% amylose by weight).

The starch is enzymatically debranched using techniques known in the art. Suitable enzymes are endo-alpha-1,6-D-glucanohydrolases, particularly pullulanase and isoamylase, more particularly isoamylase.

The amount of enzyme used is dependent upon the enzyme source and activity and base material used. For example, if isoamylase is used, typically the enzyme is used in an amount of from about 0.05 to about 10%, particularly from about 0.2 to about 5%, by weight of the starch.

The optimum parameters for enzyme activity will vary depending upon the enzyme used. The rate of enzyme degradation depends upon factors known in the art, including the enzyme type and concentration, substrate concentration, pH, temperature, the presence or absence of inhibitors, and the degree and type of modification if any. These parameters may be adjusted to optimize the digestion rate of the starch base.

The starch is gelatinized using techniques known in the art before enzyme debranching. Techniques known in the art include those disclosed for example in U.S. Pat. Nos. 4,465,702, 5,037,929, 5,131,953, and 5,149,799. Also see, Chapter XXII—"Production and Use of Pregelatinized Starch", *Starch: Chemistry and Technology*, Vol. III—Industrial Aspects, R. L. Whistler and E. F. Paschall, Editors, Academic Press, New York 1967. The gelatinization process unfolds the starch molecules from the granular structure, thereby permitting the enzyme to more easily and uniformly degrade the starch molecules.

Generally the enzyme treatment is carried out in an aqueous or buffered slurry at a starch solids level of about 10 to about 40%, depending upon the base starch being treated. A solids level of from about 15 to 35% is particularly useful, from about 18 to 30% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. For example, if isoamylase is used, a temperature of about 25 to about 70° C., particularly from about 50 to about 60° C. is typical. The pH is typically adjusted to about 4.5 to about 6.5, particularly from about 5.0 to about 6.0, using techniques known in the art.

The enzyme reaction is continued until a slowly digestible starch is achieved. In general, the enzyme reaction will take from about 1 to about 24 hours, particularly about 4 to about 12 hours. The time of the reaction is dependent upon the type of starch used, the type and amount of enzyme used, and the reaction parameters of solids percent, pH, and temperature.

The amount of hydrolysis may be monitored and defined by measuring the concentration of reducing groups which are freed by alpha-1,6-D-glucanohydrolase activity by methods well known in the art. Other techniques such as monitoring the change in viscosity, iodine reaction, or the change in molecular weight may be used to define the reaction end point. When the starch is completely debranched, the monitored measurement will no longer change. The starch may be debranched to any degree, particularly at least about 90%, more particularly at least about 95%.

Optionally, the enzyme may be deactivated (denatured) by any technique known in the art such as heat, acid or base deactivation. For example, acid deactivation may be accomplished by adjusting the pH to lower than 3.0 for at least 30 minutes or heat deactivation may be accomplished by raising the temperature to from about 80 to about 90° C. and maintaining it at that temperature for at least about 20 minutes to fully deactivate the enzyme.

The starch may also be further modified, either before or after the enzymatic hydrolysis. Such modification may be physical, enzyme, or chemical modification. Physical modification includes by shearing or thermally-inhibition, for example by the process described in U.S. Pat. No. 5,725,676.

Chemical modification includes without limitation, crosslinking, acetylation and organic esterification, hydroxyalkylation, phosphorylation and inorganic esterification, cationic, anionic, nonionic, and zwitterionic modifications, and succination. Such modifications are known in the art, for example in *Modified Starches: Properties and Uses*, Ed. Wurzburg, CRC Press, Inc., Florida (1986).

The starches may be converted, and is intended to include fluidity or thin-boiling starches prepared by oxidation, acid hydrolysis, enzyme hydrolysis, heat and or acid dextrinization. These processes are well known in the art.

Any base starch having suitable properties for use herein may be purified by any method known in the art to remove starch off flavors and colors that are native to the polysaccharide or created during processing. Suitable purification processes for treating starches are disclosed in the family of patents represented by EP 554 818 (Kasica, et al.). Alkali washing techniques are also useful and described in the family of patents represented by U.S. Pat. No. 4,477,480 (Seidel) and U.S. Pat. No. 5,187,272 (Bertalan et al.). Debranched starches may also be purified using these methods.

The resultant solution is typically adjusted to the desired pH according to its intended end use. In general, the pH is adjusted to from about 5.0 to about 7.5, particularly from about 6.0 to about 7.0, using techniques known in the art. Further, any linear chains which precipitated out of the starch dispersion may be redispersed. If purification of the debranched starch composition is desired, reaction impurities and by-products may be removed by dialysis, filtration, centrifugation or any other method known in the art for isolating and concentrating starch compositions. For example, the degraded starch may be washed using techniques known in the art to remove soluble low molecular weight fractions, such as oligosaccharides, resulting in more highly crystalline starch.

The debranched starch is allowed to crystallize by methods known in the art, for example by allowing the starch to stand and retrograde. The starch is then recovered using methods known in the art, particularly by filtration or by drying, including spray drying, freeze drying, flash drying or air drying, more particularly by filtration or flash drying. It is important to control the crystallization, typically by controlling retrogradation and drying, in order to obtain the necessary degree of crystallinity which is important to the present invention. It is further important that the method of drying and other post-crystallization processes do not substantially destroy the crystals.

The resulting starch is in the form of highly crystalline linear alpha-glucans from the debranched starch and is uniquely functional as a slowly digestible starch. The starch is characterized by a melting point temperature, $T_p$, as measured by DSC using the procedure described infra, of at least about 70° C., particularly at least about 80° C.; more particularly at least about 90° C., and an enthalpy, $\Delta H$, as measured by DSC using the procedure described infra, of at least about 25 J/g, particularly at least about 30 J/g. Such DSC values are indicative of the crystalline nature of the product.

The resultant starch is slowly digestible in that it has sustained digestion, particularly over at least a two hour time period, more particularly over at least a four hour time period, yet is significantly digested by about 6 hours after ingestion. In particular, less than about 50%, more particularly less than about 30%, is digested in the first twenty minutes following consumption and at least about 20%, particularly at least about 30%, is digested between 20 minutes and two hours following consumption, as measured using the procedure described infra. In additional, at least about 50%, particularly at least about 60%, is digested within two hours following consumption.

Starch may be consumed in its raw state, but is typically consumed after processing under high or low moisture conditions. Therefore, the invention is intended to include those starches which have the advantage of being slowly digested in the state in which it is consumed. Such state is modeled by the methods described in the examples, infra.

Further, the resultant slowly digestible starch does not produce a large rapid increase in blood glucose levels typical of high glycemic index starches, but instead provides a more moderate increase above the baseline which is sustained for a longer time period. It is also process tolerant in that the slowly digestible portion does not substantially decrease upon cooking and/or other typical food processing conditions.

The starch may be used in a variety of edible products including, but not limited to: cereal, bars, pizza, pasta, dressings, including pourable dressings and spoonable dressings; pie fillings, including fruit and cream fillings; sauces, including white sauces and dairy-based sauces such as cheese sauces; gravies; lite syrups; puddings; custards; yogurts; sour creams; beverages, including dairy-based beverages; glazes; baked goods, including crackers, breads, muffins, bagels, biscuits, cookies, pie crusts, and cakes; condiments, confectioneries and gums, and soups.

Edible products also is intended to include nutritional foods and beverages, including dietary supplements, diabetic products, products for sustained energy release such as sports drinks, nutritional bars and energy bars.

The present starch may be added in any amount desired or necessary to obtain the functionality of the composition. In general, the starch may be added in an amount of from about 0.01% to about 100%, particularly from about 1 to about 50%, by weight of the composition. The starch may be added to the food or beverage in the same manner as any other starch, typically by mixing directly into the product or adding it in the form of a sol.

EXAMPLES

The following examples are presented to further illustrate and explain the present invention and should not be taken as limiting in any regard. All percents used are on a weight/weight basis. The following test procedures are used throughout the examples:

Differential Scanning Calorimetry—Differential scanning calorimetry measurements were performed in a Perkin-Elmer DSC-7 (Norwalk, Conn., U.S.A). The instrument was calibrated with indium. Samples of approximately 10 mg starch at a starch:water ratio of 1:3 are prepared and heated at 10° C./min from 5° C. to 160° C. An empty stainless steal pan is used as a reference.

Dextrose Equivalent (DE)—For in-process DE measurement, the Fehling Volumetric Titration Method was used. A 500 ml Erlenmeyer flask was rinsed with deionized (D.I.) water. 50 ml of D.I. water was then added. The addition of 5 ml each of Fehling Solutions A and B, and 2 drops of methylene blue with two boiling chips followed. After determination of the reaction solids using a Refractometer, a starch solution containing 2–4 percent starch solids was prepared using D.I. water by diluting the reaction solution in a beaker. Before proceeding to the next step, the solids were checked by Refractometer to make sure the solution was prepared correctly. The beaker with starch solution was weighed and the weight recorded. 15 grams of the starch solution was added into the Erlenmeyer flask with prepared Fehlings solution. After they were boiled under agitation for 2 minutes on a hot plate, a bluish tint normally appeared. Starch solution from the beaker was added using a pipette gradually until the bluish tint disappeared and a distinctive reddish cuprous oxide formed. The starch solution was continuously stirred with plastic pipette to keep the solution uniform. When the reddish endpoint was reached, the beaker containing starch solution was weighed again to determine the weight of starch consumed. The calculation of D.E. can be seen from following equation:

$$D.E. = \frac{[\text{Fehling factor} \times 100]}{[(\text{grams required from starch solution}) \times (\text{conc. of starch solution})]}$$

Simulated Digestion (Englyst et al, *European Journal of Clinical Nutrition*, 1992, 46,S33–S50)—Food samples are ground/minced as if masticated. Powder starch samples are screened to a particle size of 250 microns or less. A 500–600 mg±0.1 mg of sample is weighed and added to the sample tube. 10 ml of a pepsin (0.5%), guar gum (0.5%), and HCl (0.05 M) solution is added to each tube.

Blank and glucose standard tubes are prepared. The blank is 20 ml of a buffer containing 0.25 M sodium acetate and 0.02% calcium chloride. Glucose standards are prepared by mixing 10 ml sodium acetate buffer (described above) and 10 ml of 50 mg/ml glucose solution. Standards are prepared in duplicate.

The enzyme mix is prepared by adding 18 g of porcine pancreatin (Sigma P-7545) to 120 ml of deionized water, mixing well, then centrifuging at 3000 g for 10 minutes. The supernatant is collected and 48 mg of dry invertase (Sigma I-4504) and 0.5 ml AMG 400 (Novo Nordisk) are added.

The sample tubes are pre-incubated at 37° C. for 30 min, then removed from the bath and 10 ml of sodium acetate buffer is added along with glass balls/marbles (to aid in physical breakdown of the sample during shaking).

5 ml of enzyme mixture is added to the samples, blank, and standards. The tubes are shaken horizontally in a 37° C. waterbath at approximately 180 strokes/min. Time "zero" represents the first addition of the enzyme mixture to the first tube.

After 20 and 120 minutes, 0.5-ml aliquots are removed from the incubating samples and placed into a separate tube of 20 ml 66% ethanol (to stop the reaction). After 1 hour, an aliquot is centrifuged at 3000 g for 10 minutes.

The glucose concentration in each tube is measured using the glucose oxidase/peroxidase method (Megazyme Glucose Assay Procedure GLC9/96). This is a calorimetric procedure. HPLC may also be used to detect glucose as disclosed in previous literature using this experiment.

The degree of starch digestion is determined by calculating the glucose concentration against the glucose standards, using a conversion factor of 0.9. Results are given as "% starch digested" (dry weight basis) after 20 and 120 minutes. SDS (slowly digestible starch) is the 120-minute value minus the 20-minute value.

Every sample analysis batch includes a reference sample of uncooked cornstarch. The accepted range of % digestion values for cornstarch are:

| Sample | s20 | s120 | SDS |
|---|---|---|---|
| Cornstarch[1] | 17.5 ± 2.5 | 80 ± 5 | approx. 62.5 |

[1]Melogel ® starch, commercially available from National Starch and Chemical Company, Bridgewater, NJ, USA.

Cooked models—Two general models are used to mimic commercial food processes: high moisture; and low moisture. The high moisture food model uses starch in water at 20% solids, cooked in a steam bath at 90° C. for 5 minutes. This cook is then frozen in a dry ice/acetone bath, freeze-dried, ground, and tested for digestion. The low moisture food model uses starch in water at 50% solids, and bakes the paste in an oven at 190° C. for approx. 20 minutes. The cooked starch is ground and screened to 250 microns or less and tested for the starch digestion profile.

Example 1

Preparation of Debranched and Crystallized Tapioca and Sago Starch for Digestion Study.

A. 3 kg of tapioca starch was slurried in 8423 g of water. The pH of the sample was adjusted to 5.5 using 3:1 water:HCl. The sample was jet-cooked and placed in a 59° C. water bath. When sample at 59° C., 5% pullulanase (Promozyme 200L from Novo Nordisk) was added. The sample was debranched overnight (16 hours), and then the enzyme was denatured by heating sample in a 95° C. bath for half hour. After heating, the sample was placed on bench top and crystallized overnight at room temperature with slight agitation. The product was recovered by spray drying with an inlet temperature of 210° C. and an outlet temperature of 116° C. Final D.E. of the sample was 5.3.

B. The method of Example 1A was repeated with the exception that the starch was sago starch. Final D.E. was 4.0.

C. The method of Example 1A was repeated with the exception that the tapioca starch was completely debranched using isoamylase. The reaction temperature was at 55° C. and pH was 4.0. 0.2% isoamylase (Hayashibara Inc. Japan) was added. The sample was debranched overnight (16 hours), and then the enzyme was denatured by lowering the pH to 2.0 and holding for 30 minutes. After pH was adjusted back to 6.0, the product was recovered by spray drying with an inlet temperature of 210° C. and an outlet temperature of 116° C.

These samples were also tested for digestion. Samples 1A and 1B were cooked using the low moisture model and Sample 1C remained uncooked. The samples were then tested for their digestion profile. Table 1 shows the digestion results together with the calculated SDS contents as well as the raw material DSC data.

TABLE 1

Digestion results and raw material DSC for debranched and crystallized tapioca and sago starch

| Sample | 120 | | | DSC | | | |
|---|---|---|---|---|---|---|---|
| | 20 m | m | SDS | To(° C.) | Tp(° C.) | Tc(° C.) | ΔH(J/g) |
| 1A | 40.9 | 63.0 | 22.1 | 89.7 | 106.7 | 120.0 | 24.0 |
| 1B | 47.5 | 68.4 | 20.9 | 41.0 | 76.3 | 110.8 | 34.0 |
| 1C | 36.0 | 56.5 | 26.5 | 48.8 | 86.8 | 113.6 | 33.5 |

Samples from this example showed SDS content more than 20%.

We claim:

1. A starch composition prepared from amylose-containing starch comprising crystalline linear α-glucans characterized by:
   a) at least about 20% slowly digestible starch;
   b) less than about 50% rapidly digestible starch;
   c) a melting point temperature, $T_p$ as measured by DSC, of at least about 70° C.; and
   d) an enthalpy, ΔH as measured by DSC, of at least about 25 J/g, wherein at least about 50% is digested within two hours as measured by simulated digestion.

2. The starch composition of claim 1, wherein at least about 60% is digested within two hours as measured by simulated digestion.

3. The starch composition of claim 1, whereby the starch composition is prepared from starch selected from the group consisting of maize starch, sago starch, tapioca starch, and potato starch.

4. The starch composition of claim 1, wherein the melting point temperature is at least about 80° C.

5. The starch composition of claim 1, wherein the melting point temperature is at least about 90° C.

6. The starch composition of claim 1, wherein the enthalpy is at least about 30 J/g.

7. The starch composition of claim 1, characterized by at least about 30% slowly digestible starch.

8. A process of making the starch composition of claim 1 comprising:
   a) debranching an amylose-containing starch;
   b) allowing the debranched starch to crystallize; and
   c) drying the highly crystallized debranched starch.

9. The process of claim 8, wherein the starch composition is debranched using pullulanase or isoamylase.

10. An edible product comprising the starch composition of claim 1.

11. The product of claim 10, wherein the product is a nutritional food.

* * * * *